(12) United States Patent
Kimmel et al.

(10) Patent No.: US 7,793,660 B2
(45) Date of Patent: Sep. 14, 2010

(54) METHOD OF TREATING OBSTRUCTIVE SLEEP APNEA

(75) Inventors: Steven A Kimmel, Delmont, PA (US); Gregory Yurko, Murrysville, PA (US); William A Truschel, Oakmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 278 days.

(21) Appl. No.: 11/150,380

(22) Filed: Jun. 10, 2005

(65) Prior Publication Data

US 2005/0234364 A1 Oct. 20, 2005

Related U.S. Application Data

(62) Division of application No. 10/401,633, filed on Mar. 28, 2003, now Pat. No. 6,910,481.

(51) Int. Cl.
*A61M 16/00* (2006.01)

(52) U.S. Cl. ............... 128/204.23; 128/202.22; 128/202.27; 128/204.18; 128/205.23; 128/206.21

(58) Field of Classification Search ............ 128/204.18, 128/204.21, 204.23, 200.24, 905, 920, 923, 128/304.23; 600/529, 532, 534; 434/262
See application file for complete search history.

(56) References Cited

U.S. PATENT DOCUMENTS

| | | |
|---|---|---|
| 3,898,987 A | 8/1975 | Elam |
| 3,961,624 A | 6/1976 | Weigl |
| 4,197,844 A | 4/1980 | Hartwig |
| 4,287,886 A | 9/1981 | Thompson |
| 4,366,821 A | 1/1983 | Wittmaier et al. |
| 4,444,201 A | 4/1984 | Itoh |
| 4,457,303 A | 7/1984 | Durkan |
| 4,484,578 A | 11/1984 | Durkan |
| 4,579,115 A | 4/1986 | Wallroth et al. |
| 4,619,269 A | 10/1986 | Cutler et al. |
| 4,986,269 A | 1/1991 | Hakkinen |
| 4,990,894 A | 2/1991 | Loescher et al. |
| 5,072,737 A | 12/1991 | Goulding |
| 5,233,987 A * | 8/1993 | Fabian et al. ............ 607/41 |
| 5,271,389 A | 12/1993 | Isaza et al. |
| 5,320,092 A | 6/1994 | Ryder |
| 5,335,654 A * | 8/1994 | Rapoport ............ 128/204.23 |

(Continued)

OTHER PUBLICATIONS

TSI Incorporated, "TSI Model 4040 Thermal Mass Flowmeter Rs232 Serial Command Set", Jun. 1998.

*Primary Examiner*—Tatyana Zalukaeva
*Assistant Examiner*—Clinton Ostrup
(74) *Attorney, Agent, or Firm*—Michael W. Haas

(57) ABSTRACT

A compliance monitoring system and method in which a modular compliance monitor is selectively disposed in-line in a patient circuit of a pressure support system. The monitor includes a housing having an inlet and an outlet, each of which is selectively connectable to the patient circuit so that the flow of gas in the patient circuit also passes through a passage is provided through the housing. A sensor operatively coupled to the passage detects a parameter indicative of patient breathing. A processor disposed in the housing and receives the output of the sensor and determines, from the output of the sensor, whether the patient is breathing into the patient circuit, and outputs compliance data based on this determination.

7 Claims, 1 Drawing Sheet

U.S. PATENT DOCUMENTS

| | | | |
|---|---|---|---|
| 5,363,842 A | 11/1994 | Mishelevich et al. | |
| 5,443,440 A * | 8/1995 | Tumey et al. | 601/152 |
| 5,446,449 A | 8/1995 | Lhomer et al. | |
| 5,471,977 A | 12/1995 | Olsson et al. | |
| 5,485,850 A | 1/1996 | Dietz | |
| 5,517,983 A | 5/1996 | Deighan et al. | |
| 5,546,933 A * | 8/1996 | Rapoport et al. | 128/204.23 |
| 5,549,106 A | 8/1996 | Gruenke et al. | |
| 5,603,316 A | 2/1997 | Coufal et al. | |
| 5,640,149 A | 6/1997 | Campbell | |
| 5,678,539 A | 10/1997 | Schubert et al. | |
| 5,706,801 A | 1/1998 | Remes et al. | |
| 5,715,812 A | 2/1998 | Deighan et al. | |
| 5,724,025 A | 3/1998 | Tavori | |
| 5,738,102 A | 4/1998 | Lemelson | |
| 5,832,448 A | 11/1998 | Brown | |
| 6,135,106 A * | 10/2000 | Dirks et al. | 128/204.23 |
| 6,240,921 B1* | 6/2001 | Brydon et al. | 128/205.23 |
| 6,253,764 B1* | 7/2001 | Calluaud | 128/204.18 |
| 6,651,658 B1* | 11/2003 | Hill et al. | 128/204.23 |
| 6,910,481 B2* | 6/2005 | Kimmel et al. | 128/204.23 |
| 2002/0014240 A1* | 2/2002 | Truschel | 128/204.22 |
| 2002/0165462 A1* | 11/2002 | Westbrook et al. | 600/529 |
| 2002/0195105 A1* | 12/2002 | Blue et al. | 128/204.21 |
| 2003/0213490 A1* | 11/2003 | Righetti | 128/204.18 |
| 2003/0221687 A1* | 12/2003 | Kaigler | 128/200.14 |
| 2004/0016430 A1* | 1/2004 | Makinson et al. | 128/203.12 |
| 2004/0159323 A1* | 8/2004 | Schmidt et al. | 128/204.23 |

* cited by examiner

METHOD OF TREATING OBSTRUCTIVE SLEEP APNEA

CROSS-REFERENCE TO RELATED APPLICATIONS

This application is a Divisional under 35 U.S.C. §120 of U.S. patent application Ser. No. 10/401,633, filed Mar. 28, 2003, allowed, the contents of which are incorporated herein by reference.

BACKGROUND OF THE INVENTION

1. Field of the Invention

The present invention pertains to a modular compliance monitoring apparatus for use with a conventional pressure support system that monitors whether a patient is complying with a prescribed pressure support therapy delivered by that system.

2. Description of the Related Art

Patients suffering from a pulmonary or respiratory disorder, such as obstructive sleep apnea (OSA), are often prescribed a pressure support therapy that is provided by a pressure support device, such as a continuous positive airway pressure (CPAP) device. A CPAP device delivers a flow of fluid to the airway of the patient throughout the patient's breathing cycle in order to "splint" the airway, thereby preventing its collapse during sleep. It is also known to provide a bi-level positive pressure therapy, in which the pressure of fluid delivered to the patient's airway varies or is synchronized with the patient's breathing cycle to maximize the medical effect and comfort to the patient. In a "bi-level" pressure support system, the patient receives an inspiratory positive airway pressure (IPAP) during inspiration that is greater than an expiratory positive airway pressure delivered (EPAP) during expiration.

It is further known to provide an auto-titration positive pressure therapy in which the pressure provided to the patient changes based on the detected conditions of the patient, such as whether the patient is snoring or experiencing an apnea, hypopnea, or upper airway resistance. Still other modes of providing a pressure support therapy are know, such as proportional positive airway pressure (PPAP), as taught, for example, in U.S. Pat. Nos. 5,535,738; 5,794,615; and 6,105,575 all Estes et al. and proportional assist ventilation (PAV), as taught, for example, in U.S. Pat. Nos. 5,044,362 and 5,107,830 both to Younes et al.

In treating a patient using any of the above-described pressure support systems or modes of pressure support, it is often desirable to monitor various parameters associated with the use of such systems. For example, the patient's healthcare provider, such as that patient's physician or health insurance company, is interested in ensuring that the patient actually uses the pressure support therapy as prescribed. Thus, it is known to monitor a patient's compliance with the prescribed therapy by monitoring the patient's usage of the pressure support device.

Typically, a doctor or other health care provider tracks a patient's compliance with the prescribed pressure support therapy by tracking the operation of the prescribed pressure support device. For example, U.S. Pat. Nos. 5,715,812 and 5,517,983 both to Deighan et al. teach a pressure support system that includes a built-in status monitor that determines the usage of the pressure support system by the patient. The status monitor includes a sensor, such as pressure sensor, motor current sensor, temperature sensor, or valve position sensor, that detects patient respiration and a timer that is actuated by the sensor. The timer accumulates the time of usage of the pressure support system by the patient based on the output of the sensor.

One disadvantage of the compliance monitoring system taught by these patents is the components of the compliance monitor are built-in to the pressure support system. As a result, it is not possible to readily remove or exclude the expensive components required for compliance monitoring for pressure support systems that do not require compliance monitoring.

U.S. Pat. No. 5,706,801 to Remes et al. teaches a stand-alone monitor for use with an oxygen concentrator. This monitor is not intended for use with a pressure support system that delivers a flow of gas according to prescribed modes of pressure support. The monitoring device taught by the '801 patent monitors the patient's usage of the oxygen concentrator by sensing the flow of oxygen through the monitor. At the time oxygen enriched air is detected to be flowing through the monitor, it records that time as the start of the oxygen therapy session. Conversely, when oxygen enriched air ceases flowing through the monitor, it records that time as the end of the session.

However, the monitor of the '801 patent is not capable of determining whether a patient is actually breathing into the cannula through which the oxygen flows. That is, if the oxygen concentrator is turned on and left running without the cannula being connected to the patient, the monitor taught by the '801 patent would record this as a valid session even though the oxygen is not being delivered to the patient. Thus, the monitor taught by the '801 patent is easily fooled into recording a valid session so long as the oxygen concentrator is running and providing a flow of gas through the monitor regardless of whether the patient is actually receiving the oxygen from the cannula.

SUMMARY OF THE INVENTION

Accordingly, it is an object of the present invention to provide a modular compliance monitoring system that overcomes the shortcomings of conventional compliance monitoring systems or sub-systems. This object is achieved according to one embodiment of the present invention by providing a compliance monitoring system that is modular in that it can be selectively disposed in-line in a patient circuit of a pressure support system. The monitor of the present invention includes a housing that has an inlet and an outlet, each of which is selectively connectable to the patient circuit, thereby placing the compliance monitor in-line with the patient circuit. A passage is provided through the housing that communicates the inlet with the outlet so that gas flows through the housing. A sensor is disposed within the housing and operatively coupled to the passage to detect a parameter indicative of patient breathing. Finally, a processor is disposed in the housing and receives the output of the sensor. The processor determines, from the output of the sensor, whether the patient is breathing into the patient circuit, and outputs compliance data based on this determination. Thus, the present invention provides a compliance monitor that measures compliance based on actual patient breathing so that it is not easily fooled and that can be readily used with existing pressure support systems with minimal or no retrofitting required.

It is yet another object of the present invention to provide a method of monitoring compliance that does not suffer from the disadvantages associated with conventional compliance monitoring techniques. This object is achieved by providing a method of analyzing compliance with a pressure support therapy provided by a pressure support system that includes the steps of: (1) attaching a modular compliance monitor in-line with a patient circuit by attaching a first portion of the patient circuit to an inlet of the monitor and attaching a second portion of the patient circuit to an outlet of the monitor so that gas flow through a passage in the monitor; (2) sensing a parameter indicative of patient breathing via a sensor operatively coupled to the passage; (3) determining, from the output of the sensor, whether the patient is breathing into the patient circuit; and (4) outputting compliance data based on whether or not the patient is breathing into the patient circuit.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
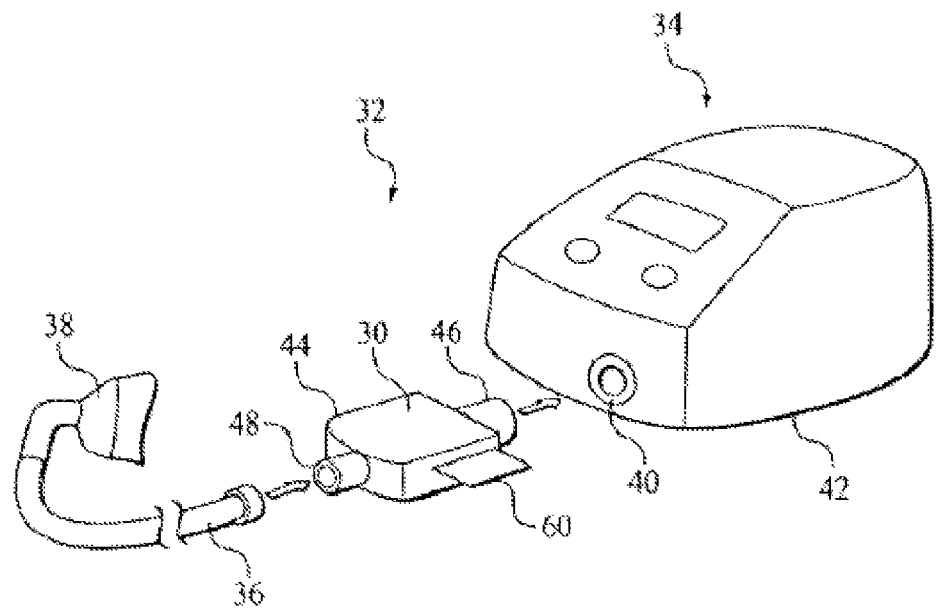
FIG. 1 is a perspective view of a modular compliance monitor for use with a pressure support system according to the principles of the present invention.

FIG. 1 is an exploded perspective view which illustrates an exemplary embodiment of a modular compliance monitor 30 for use with a conventional pressure support system, generally indicated at 32, according to the principles of the present invention. A conventional pressure support system 32 typically includes a pressure generating system 34, patient circuit 36, and a patient interface device 38 that couples the patient circuit to an airway of the patient. As shown in FIG. 1, compliance monitor 30 is adapted to be disposed in-line in a patient circuit 36.

Pressure generating system 34 receives a gas from a gas source, which is typically ambient atmosphere alone or in combination with a flow of oxygen, and outputs a flow of gas to patient circuit 36 at a pressure that is greater than atmosphere for delivery to the airway of a patient (not shown). Pressure generating system 34 commonly includes a mechanical pressure generator, such as a blower, bellows or piston, that receives ambient air, for example, at an inlet from the gas source. A pressure control system, such as a valve, a motor speed controller that controls to operating speed of the mechanical pressure generator, or both, controls the pressure of the flow of gas delivered to the patient via the patient circuit.

Patient circuit 36 is any tubing capable of carrying the gas flow from the pressure generating system to the airway of the patient. Typically, a distal portion of the patient circuit relative to pressure generating system 34 is flexible to allow for freedom of movement of the patient. Compliance monitor 30 can be provided at any location along patient circuit 36. In FIG. 1, for example, compliance monitor 30 is coupled at the proximal end of the patient circuit at an outlet coupling 40 of a housing 42 for pressure generating system 34. It is to be understood that various components may be provided in or coupled to patient circuit 36 in addition to compliance monitor 30. For example, a bacteria filter, pressure control valve, flow control valve, sensor, meter, pressure filter, humidifier and/or heater can be provided in or attached to the patient circuit.

Patient interface device 38 is any device suitable for communicating an end of patient circuit 36 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive. It should also be noted that in a single limb patient circuit, as shown, an exhaust vent is typically provided at or near patient interface device 38 to allow the patient's exhaled gasses to pass to the ambient atmosphere.

Figure 2:
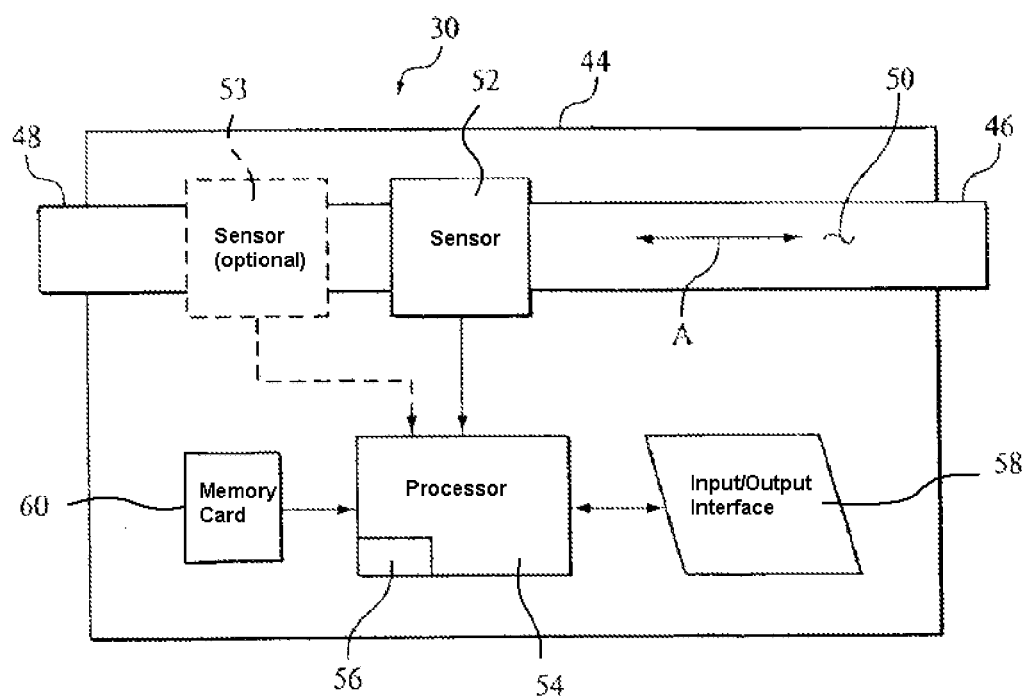
FIG. 2 is a schematic diagram of the components of the modular compliance monitor.

Referring now to FIG. 2, and with continuing reference back to FIG. 1, the details of the components of the compliance monitor and its operation will be discussed. Compliance monitor 30 includes a housing 44 having an inlet 46 and an outlet 48, both of which are selectively connectable to patient circuit 36 to place the compliance monitor in-line with the patient circuit. A passage 50 is provided through the housing communicating the inlet with the outlet so that gas flows through the housing between the inlet and the outlet, as indicated by arrow A in FIG. 2. It should be understood that there is no requirement that inlet 46 be coupled proximate to the pressure generating system and outlet 48 be coupled proximate to the patient interface device. On the contrary, these connections can be reversed, because there is no need for a unidirectional flow of gas through the monitor in order to achieve the function of the present invention.

A sensor 52 is disposed within housing 44 and operatively coupled to passage 50 so as to detect a parameter indicative of patient breathing. The present invention contemplates that sensor 52 is any device, such as a pressure sensor, a flow sensor, a microphone, or a temperature sensor, that is capable of detecting a parameter associated with the gas in passage 50 that varies when the patient is breathing into the patient circuit. The output of the sensor is provided to a processor 54, which is preferably a microprocessor capable of implementing a stored algorithm. Processor 54 preferably includes a storage area 56 to store the operating algorithm, as well as any results from implementing that algorithm.

It should be noted that the present invention contemplates providing other optional sensors 53 to monitor other parameters from the flow of gas through passage 50. It is believed that the use of multiple sensors further enhances the reliability of the breathing detection. Of course, it also adds to the complexity and cost of the device.

The present invention further contemplates that compliance monitoring system 30 includes an input/output interface 58 for communicating, information, data and/or instructions and any other communicatable items, collectively referred to as "data", between a user and processor 54. Examples of common input/output interfaces suitable for this purpose include a keypad and display. Other communication techniques, either hard-wired or wireless, are also contemplated by the present invention. For example, the present invention contemplates providing a smart card terminal that enables data to be loaded into processor 54 from a removable smart card 60 (See FIG. 1) or loaded onto the smart card from the processor. Other exemplary, interface devices and techniques adapted for use with the pressure support system include, but are not limited to, an RS-232 port, CD reader/writer, DVD reader/writer, RF link, modem (telephone, cable or other). In short, any conventional technique for providing, receiving, or exchanging data with processor 54 are contemplated by the present invention as input/output device 58.

The components of compliance monitor 30 are powered using any conventional technique. For example, an external power supply and/or a battery can be provided to power the elements of the compliance monitor.

Processor 54 receives the output from sensor 52 (as well as any other optional sensors 53) and determines from this output whether the patient is breathing into the patient circuit. The present invention contemplates that this determination can be done in any conventional manner. For example, if sensor 52 is a pressure or flow sensor, processor 54 monitors the pressure or flow signal to look for variations in this signal that are above thresholds, which are set such that any signal exceeding the threshold would indicate breathing by the patient into the patient circuit. The processor can also monitor the output of the sensor or sensors to look for changes, variations, or patterns that are indicative of a patient breathing into the patient circuit. In short, the present invention contemplates using any technique for detecting breathing based on the output of one or more sensors. Examples of other techniques for detecting breathing include monitoring the temperature and/or the humidity of the gas passing through monitor 30 or monitoring the concentration of one or more gas constituents, such as carbon dioxide concentration or oxygen concentration, of the gas passing through the monitor. The present invention also contemplates using multiple techniques for detecting breathing to increase the reliability of this determination.

If the processor determines that the patient is breathing into the patient circuit, it outputs compliance data based on this determination. Outputting the compliance data can be done in many ways. For example, the compliance data can be stored in memory 56 associated with processor 54, stored in another storage device such as a ROM, RAM, EPROM, disk, smart card associated with the processor, or output via input/output interface 58.

It is to be further understood that the compliance data output by the processor can take many forms. For example, one embodiment of the present invention contemplates that the compliance data includes a start time at which breathing is detected, an end time at which breathing ceases to be detected, or both. In this case, the total compliance time, i.e., the total amount of time that the device is used during a usage session, is determined by calculating the total usage time from the end time and the start time. A real time clock 60 associated with processor 54 is provided for indicating the start time and end time when the events that give rise to a start of usage or an end of usage are detected.

A second embodiment of the present invention contemplates that the compliance data includes a time duration during which breathing was detected, a time duration during which breathing is not detected, or both. In this embodiment, the time at which breathing is detected starts a timer, such as clock 60, and the time at which breathing is no longer detects stops the timer.

An example of a compliance monitoring technique suitable for use with the present invention includes that described in U.S. Patent Appln. No. 60/406,247 to Yurko et al., the contents of which are incorporated herein by reference.

The present invention also contemplates that processor 54 can monitor a number of other parameters, in addition to an indication of the patient's breathing on the pressure support system. For example, the flow, volume, pressure, and/or temperature of the flow of gas through the compliance monitor can be monitored. In addition, the sounds generated by the patient, such as breathing sounds and snoring can be detected by the compliance monitor. This information can be output by input/output interface 58.

The present invention also contemplates storing alarm thresholds in the compliance monitor, such as in memory 56 or in another storage device such as a ROM, RAM, EPROM, disk, smart card associated with the processor, or output via input/output interface 58. The thresholds can be set via input/output interface 58 is set at the time of manufacture.

Processor 56 compares a monitored parameter from sensor 52, as well as a parameter from any optional sensor, with the alarm threshold and outputs an alarm signal responsive to the alarm threshold being met by the monitored parameter. The alarm signal and/or the parameter causing the alarm can be stored in a memory, output to a remote location via input/output interface 58, or can cause a human perceivable format, such as an audio or visual alarm. The alarm thresholds completed by the present invention include over temperature, high pressure, low pressure, low respiratory rate, high respiratory rate, low minute ventilation, high minute ventilation, high tidal volume, low tidal volume, low system leak, high system leak, or any combination thereof.

The following is a brief summary of the use of modular compliance monitor 30. First, the compliance monitor is attached in-line with patient circuit 36 by attaching a first portion of the patient circuit to inlet 46 of the monitor and attaching a second portion of the patient circuit to outlet 48 so that gas flow through passage 50 in the monitor between the inlet and the outlet. The compliance monitor is then activated so that processor 54 begins monitoring a parameter indicative of patient breathing based on the output of sensor 52 to determine whether a patient is breathing into the patient circuit. Processor output compliance data based on whether or not such a patient is breathing into the patient circuit.

In a further embodiment, the compliance data is sent from the monitor to a remote location via a communication link, stored on a data storage device removably coupled to the monitor, visually displayed on a display provided on the monitor, or any combination thereof. Yet another embodiment of the present invention contemplates setting the alarm threshold via an input device, monitoring a parameter that is based on an output of sensor 52, comparing the parameter with the alarm threshold in processor 54, and outputting an alarm signal from the processor if the alarm threshold is met by the monitored parameter. The present invention also contemplates monitoring a parameter associated with a flow of gas in the passage based on an output of the sensor and outputting the parameter via input/output interface 58 so that data other than the compliance data is generated by the compliance monitor.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A method of treating obstructive sleep apnea comprising the steps of:

providing a pressure support system that includes, a first housing, a pressure generator disposed in the housing, a patient circuit having a first end coupled to an outlet of the pressure generator, and a patient interface device coupled to a second end of the patient circuit;

delivering a pressure support therapy to a patient to treat obstructive sleep apnea using the pressure support system;

providing a modular compliance monitor that includes a second housing separate from the first housing, wherein the second housing includes an inlet, an outlet, and a passage defined through the second housing from the inlet to the outlet, the modular compliance monitor including a sensor disposed within the second housing and operatively coupled to the passage, and a processor disposed within the second housing and operatively coupled to the sensor, the processor being adapted to: (i) determine from an output of the sensor whether the patient is breathing into the patient circuit, and (ii) generate compliance data indicative of usage of the pressure support system based on the determination of whether the patient is breathing into the patient circuit;

removeably attaching the modular compliance monitor in-line with the patient circuit by attaching a first portion of the patient circuit to the inlet of the modular compliance monitor and attaching a second portion of the patient circuit to the outlet of the modular compliance monitor so that gas flows through the passage between the inlet of the modular compliance monitor and the outlet of the modular compliance monitor;

sensing a parameter indicative of patient breathing via the sensor;

determining in the processor from the sensed parameter whether the patient is breathing into the patient circuit;

generating in the processor compliance data indicative of usage of the pressure support system by the patient to provide the pressure support therapy based on an outcome of the determining, the compliance data comprising a total amount of time that the pressure support system was used by the patient in a usage session; and outputting the generated compliance data from the processor.

2. The method of claim 1, wherein sensing a parameter indicative of patient breathing includes sensing a pressure, a flow, a sound, a gas concentration sensor, a humidity sensor or a temperature.

3. The method of claim 1, further comprising:
setting an alarm threshold via an input device;
monitoring a parameter that is based on an output of the sensor;
comparing the parameter with the alarm threshold; and
outputting an alarm signal responsive to the alarm threshold being met by the monitored parameter.

4. The method of claim 1, wherein outputting the compliance data comprises:
sending the compliance data from the compliance monitor to a remote location via a communication link;
storing the compliance data on a data storage device removably coupled to the compliance monitor;
visually displaying the compliance data on a display provided on the compliance monitor; or
any combination thereof.

5. The method of claim 1, further comprising:
monitoring a parameter associated with a flow of gas in the passage based on an output of the sensor; and
outputting the parameter.

6. The method of claim 1, wherein outputting the compliance data includes providing a start time at which breathing into the patient circuit is detected, an end time at which breathing into the patient circuit ceases to be detected, or both.

7. The method of claim 1, wherein outputting the compliance data includes providing a time duration during which breathing into the patient circuit was detected, a time duration during which breathing into the patient circuit is not detected, or both.

* * * * *